（12） United States Patent
Coupard et al.

(10) Patent No.: US 9,085,502 B2
(45) Date of Patent: Jul. 21, 2015

(54) PROCESS FOR DEHYDRATION OF ETHANOL INTO ETHYLENE WITH LOW ENERGY CONSUMPTION

(75) Inventors: Vincent Coupard, Villeurbanne (FR); Natacha Touchais, Vienne (FR); Stephanie Fleurier, Lyons (FR); Helena Gonzalez Penas, Lyons (FR); Walter Vermeiren, Houthalen-Helchteren (BE); Delphine Minoux, Nivelles (BE); Philip De Smedt, Sint-Niklaas (BE); Cindy Adam, Wierde (BE)

(73) Assignees: TOTAL PETROCHEMICALS RESEARCH FELUY, Seneffe (Feluy) (BE); IFP ENERGIES NOUVELLES, Rueil-Malmaison Cedex (FR)

( * ) Notice: Subject to any disclaimer, the term of this patent is extended or adjusted under 35 U.S.C. 154(b) by 357 days.

(21) Appl. No.: 13/554,199

(22) Filed: Jul. 20, 2012

(65) Prior Publication Data

US 2013/0190547 A1    Jul. 25, 2013

(30) Foreign Application Priority Data

Jul. 21, 2011  (FR) .................................... 11/02.274
Aug. 8, 2011   (FR) .................................... 11/02.482

(51) Int. Cl.
C07C 1/24      (2006.01)
C07C 7/04      (2006.01)

(52) U.S. Cl.
CPC .... *C07C 1/24* (2013.01); *C07C 7/04* (2013.01)

(58) Field of Classification Search
CPC ......................................................... C07C 1/24
USPC .......................... 585/638, 639, 640, 641, 642
See application file for complete search history.

(56) References Cited

U.S. PATENT DOCUMENTS 4,232,179 A * 11/1980 Valladares Barrocas
                         et al. ............................. 585/640
4,396,789 A    8/1983 Barrocas et al.
2012/0101320 A1  4/2012 Stewart et al.

FOREIGN PATENT DOCUMENTS

WO  2007/134415 A2  11/2007
WO  2011/002699 A1   1/2011

OTHER PUBLICATIONS

Search Report and Written Opinion, dated Mar. 1, 2012, issued in corresponding FR 11/02.274.
Search Report and Written Opinion, dated Mar. 1, 2012, issued in corresponding FR 11/02.482.

* cited by examiner

*Primary Examiner* — In Suk Bullock
*Assistant Examiner* — Sharon Pregler
(74) *Attorney, Agent, or Firm* — Millen, White, Zelano & Branigan, P.C.

(57) ABSTRACT

A process for dehydration of an ethanol feedstock into ethylene, comprising the vaporization of said ethanol feedstock in a mixture with at least a portion of the recycled purified water stream from heat exchange with the effluent that is obtained from the last reactor.

16 Claims, 1 Drawing Sheet

PROCESS FOR DEHYDRATION OF ETHANOL INTO ETHYLENE WITH LOW ENERGY CONSUMPTION

FIELD OF THE INVENTION

This invention relates to a process for transformation of ethanol into ethylene and in particular to a process for dehydration of ethanol.

PRIOR ART

The reaction of dehydration of ethanol into ethylene is known and has been presented in detail since the end of the 19th century. It is known that this reaction is very endothermic, balanced, and shifted toward ethylene at high temperature. The temperature drop that corresponds to the total conversion of pure ethanol is 380° C. The reference catalyst that is often used is a monofunctional acid catalyst. The gamma-alumina is the most cited catalyst. "The Dehydration of Alcohols over Alumina. I: The Reaction Scheme," H. Knözinger, R. Köhne, Journal of Catalysis (1966), 5, 264-270 is considered to be the basic publication on the works on dehydration of alcohols including ethanol. The zeolites are also used for this application, and in particular ZSM5 from the 1980s, such as, for example, in "Reactions of Ethanol over ZSM-5," S. N. Chaudhuri & al. Journal of Molecular Catalysis 62: 289-295 (1990).

The U.S. Pat. No. 4,232,179 describes a process for dehydration of ethanol into ethylene in which the heat that is necessary to the reaction is supplied by the introduction into the reactor of a coolant mixed with the feedstock. The coolant is either water vapor that is obtained from an outside source, or an outside stream that comes from the process, or the recycling of a portion of the effluent of the dehydration reactor, i.e., the ethylene that is produced. The introduction of the mixture of the feedstock with said coolant makes it possible to provide the heat that is necessary for keeping the temperature of the catalytic bed at a compatible level with the desired conversion levels. In the case where the coolant is the effluent from the dehydration reactor, a compressor for recycling said effluent is necessary. However, the recycling of the ethylene that is produced by the reaction is a drawback because the introduction of ethylene modifies the balance of the dehydration reaction. In addition, the ethylene participates in secondary oligomerization reactions, transfer of hydrogen and disproportionation of olefins that are reactions of an order that is higher than 0 relative to their reagent. The increase in the ethylene concentration from the beginning of the reaction multiplies the formation of secondary products. The loss of ethylene is therefore more significant, which reflects a lowering of selectivity.

The patent application WO 2007/134415 A2 describes a process for dehydration of ethanol into ethylene that is improved relative to that of the U.S. Pat. No. 4,232,179 that makes possible a reduced investment cost, owing to a reduced number of pieces of equipment and a reduced operational cost, owing to the non-use of water vapor external to the process. In this process, at least a portion of the effluent of the dehydration reactor (mixture of ethylene that is produced and water vapor) and the superheated water vapor obtained from the water that is produced by the dehydration of ethanol and condensed in the reactor are used as a coolant and enter within the dehydration reactor by mixing with ethanol. Furthermore, said patent application is silent on the pressure condition that is to be complied with between the ethanol feedstock and the effluent for the purpose of maximizing the heat exchange.

The U.S. Pat. No. 4,396,789 also describes a process for dehydration of ethanol into ethylene in which the ethanol and the water vapor acting as coolant are introduced into the first reactor at a temperature that is between 400 and 520° C. and at a high pressure of between 20 and 40 atm, in such a way that the effluent produced by the dehydration reaction is drawn off from the last reactor at a pressure that is at least higher than 18 atm, said reaction product, i.e., ethylene, after cooling, being able to undergo the final cryogenic distillation stage without an intermediate compression stage. Said process is also characterized by a heat exchange between said product of the dehydration reaction and the feedstock that is introduced into the first reactor, said reaction product being used for vaporizing the feedstock that comes into the first reactor. The unreacted ethanol, at least a portion of the water that is formed during the reactions of the process, and the water that is added for the final washing of gases are recycled to ensure the complete conversion of the ethanol.

One objective of the invention is to provide a process for dehydration of ethanol into ethylene in which the feedstock is introduced into stage a) for vaporization of the feedstock at low pressure, less than the reaction pressure, such that said process does not require any coolant that is external to the process. In particular, the feedstock is introduced into stage a) for vaporization of the feedstock at a pressure that is lower than that of the effluent at the outlet of the last reactor so as to maximize the heat exchange between the feedstock and the effluent that is obtained from the last reactor, i.e., to exchange the entire vaporization enthalpy of the feedstock and the condensation enthalpy of said effluent.

Another objective of the invention is to provide a process for dehydration of ethanol into ethylene of high purity, whereby said process makes it possible to increase the selectivity of ethylene with a specific consumption per ton of ethylene that is produced that is significantly lowered relative to the processes of the prior art.

SUMMARY AND ADVANTAGE OF THE INVENTION

The invention describes a process for dehydration of an ethanol feedstock into ethylene comprising:

a) The vaporization of said ethanol feedstock that is mixed with at least a portion of the purified water stream that is recycled according to stage f) in an exchanger owing to an exchange of heat with the effluent that is obtained from the last reactor, said ethanol feedstock that is mixed with at least a portion of said purified water stream being introduced into said vaporization stage at a pressure of between 0.1 and 0.4 MPa, b) The compression of said feedstock that is vaporized in a compressor, c) Introduction of said vaporized and compressed feedstock, at an entrance temperature of between 350 and 500° C. and at an entrance pressure of between 0.2 and 1.3 MPa, in at least one adiabatic reactor that contains at least one dehydration catalyst and in which the dehydration reaction takes place, d) The separation of the effluent that is obtained from the last adiabatic reactor of stage c) into an effluent that comprises ethylene at a pressure that is lower than 1 MPa and an effluent that comprises water, e) The purification of at least a portion of the effluent that comprises water that is obtained from stage d) and the separation of at least one stream of purified water and at least one stream of unconverted ethanol, f) The recycling of at least a portion of the stream of purified water obtained from stage e) upstream from stage a).

This invention offers the advantage relative to the processes of the prior art for maximizing the heat exchange between the feedstock and the effluent that is obtained from the last reactor, i.e., to exchange the entire vaporization enthalpy of the feedstock and the major portion of the condensation enthalpy of said effluent owing to the introduction of the feedstock into the vaporization stage a) at a pressure that is lower than that of the effluent at the outlet of the last reactor.

DESCRIPTION OF THE INVENTION

The ethanol feedstock that is treated in the process according to the invention is optionally obtained by a process for the synthesis of alcohol from fossil resources, such as, for example, from carbon, natural gas, or carbon waste.

Said feedstock can also advantageously come from non-fossil resources. Preferably, the ethanol feedstock that is treated in the process according to the invention is an ethanol feedstock that is produced from a renewable source that is obtained from the biomass and is often called "bioethanol." Said ethanol feedstock is a feedstock that is produced by biological means, preferably by fermentation of sugar obtained from, for example, sugar-producing crops such as sugarcane (saccharose, glucose, fructose and sucrose), beet scraps, or else amylase plants (starch), or lignocellulosic biomass or hydrolyzed cellulose (majority glucose and xylose, galactose), containing variable amounts of water.

Said feedstock is advantageously obtained by fermentation from three sources: 1) The sucrose from cane sugar or beet scraps, 2) The starch that is present in the grains and the tubers, and 3) The cellulose and hemicellulose that are present in the wood, the herbs and other lignocellulosic biomasses, starch, cellulose and hemicellulose having to be hydrolyzed into sugars before undergoing a fermentation stage.

For a more complete description of the standard fermenting processes, it is possible to refer to the work 'Les Biocarburants, Etat des lieux, perspectives et enjeux du développement [The Biofuels: Assessment, Perspectives and Development Issues], Daniel Ballerini, Editions Technip.'

Said feedstock can advantageously also be obtained by fermentation of synthesis gas. Said feedstock can also advantageously be obtained by hydrogenation of the corresponding acids or esters. In this case, the acetic acid or the acetic esters are advantageously hydrogenated using hydrogen in ethanol. The acetic acid can advantageously be obtained by carbonylation of methanol or by fermentation of the carbohydrates. Preferably, the ethanol feedstock that is treated in the process according to the invention is an ethanol feedstock that is produced from a renewable source that is obtained from the biomass.

The ethanol feedstock that is used according to the invention is advantageously a concentrated, hydrated, ethanol feedstock. Concentrated, hydrated, ethanol feedstock is defined as an ethanol feedstock that comprises a percent by mass of ethanol that is greater than or equal to 35% by weight. Preferably, said concentrated ethanol feedstock comprises a percent by mass of ethanol of between 35 and 99.9% by weight. In a preferred manner, said concentrated ethanol feedstock comprises a percent by mass of ethanol of between 35 and 96% by weight. Said concentrated ethanol feedstock also advantageously comprises, in addition to water, a content of alcohols other than ethanol, such as, for example, methanol, butanol and/or isopentanol that is less than 10% by weight, and preferably less than 5% by weight, a content of oxidized compounds other than the alcohols such as, for example, ethers, acids, ketones, aldehydes, and/or esters that are advantageously less than 1% by weight, and a nitrogen and sulfur content, organic and mineral, advantageously less than 0.5% by weight, with the percentages by weight being expressed relative to the total mass of said feedstock.

The ethanol feedstock that is used according to the invention advantageously undergoes a pretreatment stage prior to the vaporization stage a) of said feedstock. Said pretreatment stage makes it possible to eliminate the impurities that are contained in said feedstock in such a way as to limit the deactivation of the dehydration catalyst that is placed downstream, and in particular the compounds that contain nitrogen and the compounds that contain sulfur. The oxidized compounds that are present in said feedstock are not substantially eliminated.

Said pretreatment stage is advantageously implemented by means that are known to one skilled in the art, such as, for example, the use of at least one resin, by the adsorption of impurities on solids preferably at a temperature of between 20 and 60° C., by a concatenation that comprises a first hydrogenolysis stage that operates at a temperature of between 20 and 80° C., followed by a stage for recovery on acid solid at a temperature of between 20 and 80° C. and/or by distillation. In the case of the use of at least one resin, said resin is preferably acid and is used at a high temperature of between 70 and 200° C. Said resin can optionally be preceded by a basic resin.

In the case where the pretreatment stage is implemented by the adsorption of impurities on solids, said solids are advantageously selected from among the molecular sieves, activated carbon, alumina and zeolites.

Said pretreatment stage of the ethanol feedstock makes it possible to produce a purified ethanol fraction in which the organic impurities have been eliminated, so as to obtain a purified feedstock that responds to the level of impurities that are compatible with the dehydration catalyst.

Stage a)

According to the invention, the dehydration process comprises a stage a) for vaporization of said ethanol feedstock, optionally pretreated, mixed with at least a portion of the purified water stream that is recycled according to stage f), in an exchanger owing to a heat exchange with the effluent that is obtained from the last adiabatic reactor, with said ethanol feedstock, mixed with at least a portion of the purified water stream that is recycled according to stage f) being introduced into said vaporization stage at a pressure of between 0.1 and 0.4 MPa.

Preferably, at least one unreacted ethanol stream that is obtained from stage e) for purification of the effluent that comprises water is also introduced, mixed with said ethanol feedstock, optionally pretreated, and mixed with at least a portion of the purified water stream that is recycled according to stage f), in the exchanger of the evaporation stage a).

Preferably, said ethanol feedstock is mixed with at least a portion of the purified water stream that is recycled according to stage f) and with at least one unreacted ethanol stream that is obtained from stage e) for purification of the effluent comprising water, after the pretreatment stage of said ethanol feedstock.

Preferably, said ethanol feedstock, mixed with at least a portion of the purified water stream that is recycled according to stage f) and optionally mixed with at least one unreacted ethanol stream that is obtained from stage e), is introduced into said vaporization stage a) at a pressure that is lower than the pressure of the effluent at the outlet of the last reactor.

An essential criterion of this invention is the adjustment of the pressure upstream from the vaporization stage a) of said ethanol feedstock that is mixed with at least a portion of the purified water stream that is recycled according to stage f) and optionally mixed with at least one unreacted ethanol stream that is obtained from stage e), in such a way as to maximize the heat exchange between the mixture of said feedstock and different streams and the effluent that is obtained from the last adiabatic reactor. The introduction of said ethanol feedstock mixed with at least a portion of the purified water stream that is recycled according to stage f) and optionally mixed with an unreacted ethanol stream that is obtained from stage e), in the vaporization stage a) at this specific pressure level between 0.1 and 0.4 MPa, lower than the pressure of the effluent at the outlet of the last reactor, makes it possible to benefit from a vaporization temperature of the feedstock mixture that is lower than the condensation temperature of the effluent that is obtained from the last adiabatic reactor. Thus, the major portion of the latent heat of the aqueous phase of the effluent that is obtained from the last adiabatic reactor is recovered for vaporizing said mixture from said feedstock and different streams, without an external heat supply. The entire vaporization enthalpy of said mixture of said feedstock and different streams is therefore exchanged with the condensation enthalpy of said effluent.

The pressure of said ethanol feedstock, mixed with at least a portion of the purified water stream that is recycled according to stage f) and optionally mixed with at least one unreacted ethanol stream that is obtained from stage e), at its vaporization is advantageously selected in such a way that the temperature difference between the effluent that is obtained from the last adiabatic reactor that is condensed and said feedstock mixture that evaporates is always at least higher than 2° C., and preferably at least higher than 3° C.

Stage b)

According to the invention, said ethanol feedstock that is mixed with at least a portion of the purified water stream that is recycled according to stage f) and optionally mixed with at least one unreacted ethanol stream that is obtained from stage e), vaporized, undergoes compression in a compressor. Compression stage b) is advantageously implemented in any type of compressor that is known to one skilled in the art. In particular, compression stage b) is advantageously implemented in a compressor of the radial compressor type with an integrated multiplier or in a compressor that comprises one or more fans with a radial wheel that are arranged in series without intermediate cooling.

Compression stage b) of said ethanol feedstock that is mixed with at least a portion of the purified water stream that is recycled according to stage f) and optionally mixed with at least one unreacted ethanol stream that is obtained from stage e), vaporized, makes it possible to prevent the supply of coolant that is external to the process for ensuring the vaporization of said mixture of said feedstock and different streams. Thus, only the streams that are obtained from the process are used. Compression stage b) therefore makes it possible to produce a heat pump that is integrated with said process, using the streams that are obtained from the process, and not involving external coolant.

The combination of the specific operating conditions of stage a) and stage b) makes it possible to recover the major portion of the latent heat of the aqueous phase of the effluent that is obtained from the last adiabatic reactor for vaporizing the ethanol feedstock that is mixed with at least a portion of the purified water stream that is recycled according to stage f) and optionally mixed with at least one unreacted ethanol stream that is obtained from stage e), without supply of external heat, i.e., exchanging the entire vaporization enthalpy of said mixture of said feedstock and different streams and the major portion of the condensation enthalpy of said effluent.

The pressure of said ethanol feedstock that is mixed with at least a portion of the purified water stream that is recycled according to stage f) and optionally mixed with at least one unreacted ethanol stream that is obtained from stage e), vaporized at the end of the compression stage b), is advantageously between 0.2 and 1.3 MPa. The exit pressure of said mixture of said feedstock and different streams is adequate for producing the temperature condition that is necessary to the exchange of stage a): in stage a), the vaporization temperature of said mixture of said feedstock and different streams is to be lower than the condensation temperature of the effluent that is obtained from the last reactor.

Said ethanol feedstock that is mixed with at least a portion of the purified water stream that is recycled according to stage f) and optionally mixed with at least one unreacted ethanol stream that is obtained from stage e), vaporized and compressed, obtained from compression stage b), is optionally heated in a gas single-phase-type exchanger, owing to a heat exchange with the effluent that is obtained from the last adiabatic reactor of stage c). In said gas single-phase-type exchanger, said mixture of said feedstock and different streams, vaporized and compressed, is superheated, and the effluent that is obtained, in the gaseous state, from the last adiabatic reactor of stage c) is "de-superheated" without being condensed.

Said mixture of said feedstock and different streams is advantageously superheated to a temperature of between 250 and 375° C. and preferably between 280 and 360° C. At the end of said gas single-phase-type exchanger, the effluent that is obtained, in the gaseous state, from the last adiabatic reactor of stage c) advantageously has a temperature of between 180 and 220° C. Thus, the use of different exchangers, of the gas single-phase-type and the gas/liquid vaporizer-type, and vaporization, at a pressure that is lower than that of the output effluent of the last reactor, of said ethanol feedstock mixed with at least a portion of the purified water stream that is recycled according to stage f) and optionally mixed with at least one unreacted ethanol stream that is obtained from stage e), makes possible the condensation of at least 80% of the water vapors that are present in the effluent that is obtained from the last reactor.

Said mixture of feedstock—vaporized, compressed and optionally heated in said gas single-phase-type exchanger—is next advantageously introduced into a furnace in such a way as to bring it to an entrance temperature in at least one adiabatic reactor that is compatible with the temperature of the dehydration reaction.

Stage c)

According to the invention, said ethanol feedstock that is mixed with at least a portion of the purified water stream that is recycled according to stage f) and optionally mixed with at least one unreacted ethanol stream that is obtained from stage e), vaporized and compressed, and optionally heated, is introduced at an entrance temperature of between 350 and 500° C. and at an entrance pressure of between 0.2 and 1.3 MPa in at least one adiabatic reactor that contains at least one fixed bed of dehydration catalyst and in which the dehydration reaction takes place.

The effluent that is obtained from the last adiabatic reactor of stage c) advantageously has, at the outlet of the last adiabatic reactor of stage c), a temperature of between 270 and 420° C. and preferably between 300 and 410° C.

The effluent that is obtained from the last adiabatic reactor of stage c) advantageously offers, at the outlet of the last adiabatic reactor of stage c), a pressure of between 0.1 and 1.1 MPa.

Stage c), in which the dehydrogenation reaction takes place, is advantageously carried out in one or two reactors.

In the case where stage c) is implemented in an adiabatic reactor, said ethanol feedstock that is mixed with at least a portion of the purified water stream that is recycled according to stage f) and optionally mixed with at least one unreacted ethanol stream that is obtained from stage e), vaporized and compressed, and optionally heated, is advantageously introduced into said reactor at an entrance temperature of between 400 and 500° C. and at an entrance pressure of between 0.2 and 1.2 MPa. The effluent that is obtained from said adiabatic reactor advantageously has a temperature that is between 300 and 400° C. and an exit pressure that is advantageously between 0.1 and 1.1 MPa.

In the case where stage c) is implemented in two adiabatic reactors, said ethanol feedstock that is mixed with at least a portion of the purified water stream that is recycled according to stage f) and optionally mixed with at least one unreacted ethanol stream that is obtained from stage e), vaporized and compressed, and optionally heated, is advantageously introduced into the first reactor at an entrance temperature of between 350 and 450° C. and preferably at a temperature of between 370 and 420° C., and at an entrance pressure of between 0.3 and 1.3 MPa and preferably between 0.4 and 0.8 MPa.

The effluent that is obtained from the first adiabatic reactor advantageously exits from said first reactor at a temperature of between 290 and 390° C. and at a pressure of between 0.2 and 1.2 MPa.

Said effluent is next advantageously introduced into a furnace in such a way that the entrance temperature of said effluent in the second adiabatic reactor is between 350 and 450° C. and preferably between 370 and 430° C. Said effluent has an entrance pressure in said second reactor that is advantageously between 0.2 and 1.2 MPa and preferably between 0.3 and 0.7 MPa.

The effluent that is obtained from the second adiabatic reactor exits from said second adiabatic reactor at a temperature that is advantageously between 310 and 410° C. The exit pressure of said effluent that is obtained from the second adiabatic reactor is advantageously between 0.1 and 1.1 MPa.

The entrance temperature of the reactor(s) can advantageously be gradually increased to prevent the deactivation of the dehydration catalyst.

The dehydration reaction that takes place in at least one adiabatic reactor of stage c) of the process according to the invention is advantageously performed at an hourly speed by weight that is between 0.1 and 20 h−1 and preferably between 0.5 and 15 h−1. The hourly speed by weight is defined as being the ratio of the mass flow rate of the pure ethanol feedstock to the mass of the catalyst.

The dehydration catalyst that is used in stage c) is a catalyst that is known to one skilled in the art. Said catalyst is preferably an amorphous acid catalyst or a zeolitic acid catalyst. In the case where the dehydration catalyst that is used in stage c) is a zeolitic catalyst, said catalyst comprises at least one zeolite that is selected from among the zeolites that have at least pore openings containing 8, 10 or 12 oxygen atoms (8 MR, 10 MR or 12 MR). It is actually known to define the size of the pores of the zeolites by the number of oxygen atoms that form the annular cross-section of the channels of the zeolites, called "member ring" or MR in English. In a preferred manner, said zeolitic dehydration catalyst comprises at least one zeolite that has a structural type that is selected from among the structural types MFI, MEL, FAU, MOR, FER, SAPO, TON, CHA, EUO and BEA. Preferably, said zeolitic dehydration catalyst comprises an MFI-structural-type zeolite and in a preferred manner a ZSM-5 zeolite.

The zeolite that is implemented in the dehydration catalyst that is used in stage c) of the process according to the invention can advantageously be modified by dealuminification or desilication according to any method of dealuminification or desilication known to one skilled in the art.

The zeolite that is implemented in the dehydration catalyst that is used in stage c) of the process according to the invention or the final catalyst can advantageously be modified by an agent of the type to attenuate its total acidity and to improve its hydrothermal resistance properties. Preferably, said zeolite or said catalyst advantageously comprises phosphorus, preferably added in $H_3PO_4$ form following a vapor treatment after neutralization of the excess acid by a basic precursor, such as, for example, sodium Na or calcium Ca. In a preferred manner, said zeolite comprises a phosphorus content of between 2.5 and 4.5% by weight relative to the total mass of the catalyst.

Preferably, the dehydration catalyst that is used in stage c) of the process according to the invention is the catalyst that is described in the patent applications WO/2009/098262, WO/2009/098267, WO/2009/098268 or WO/2009/098269.

In the case where the dehydration catalyst that is used in stage c) is an amorphous acid catalyst, said catalyst comprises at least one porous refractory oxide that is selected from among alumina, alumina that is activated by a deposit of mineral acid, and silica-alumina.

Said amorphous or zeolitic dehydration catalyst that is used in stage c) of the process according to the invention can advantageously also comprise at least one oxide-type matrix that is also called a binder. According to the invention, matrix is defined as an amorphous or poorly crystallized matrix. Said matrix is advantageously selected from among the elements of the group that is formed by clays (such as, for example, among the natural clays such as kaolin or bentonite), magnesia, aluminas, silicas, silica-aluminas, aluminates, titanium oxide, boron oxide, zirconia, aluminum phosphates, titanium phosphates, zirconium phosphates, and carbon. Preferably, said matrix is selected from among the elements of the group that is formed by the aluminas, the silicas, and the clays.

Said dehydration catalyst that is used in stage c) of the process according to the invention is advantageously shaped in the form of grains of different shapes and sizes. It is advantageously used in the form of cylindrical or multilobar extrudates such as bilobar, trilobar and multilobar extrudates of straight or twisted shape, but can optionally be manufactured and used in the form of crushed powder, tablets, rings, balls, wheels, or spheres. Preferably, said catalyst is in the form of extrudates.

Said dehydration catalyst that is used in stage c) of the process according to the invention is advantageously implemented in at least one reactor, in a fixed bed or in a moving bed.

In stage c) of the process according to the invention, the catalysts that are used and the operating conditions are selected in such a way as to maximize the production of ethylene. The overall dehydration reaction that is implemented in stage c) of the process according to the invention is as follows:

The conversion of the ethanol feedstock in stage c) is advantageously greater than 90%, preferably 95%, and in a preferred manner greater than 99%.

The conversion of the ethanol feedstock is defined, in percentage, by the following formula: [1−(hourly output mass of ethanol/hourly input mass of ethanol)]×100.

The hourly input and output mass of ethanol is measured conventionally by gas phase chromatography of the aqueous phase.

Stage c), in which the dehydration reaction takes place, is advantageously carried out in one or two reactors. A preferred reactor is a radial reactor that operates in upward or downward mode. During stage c) of the process according to the invention, the transformation of the feedstock is accompanied by the deactivation of the dehydration catalyst by coking and/or by adsorption of inhibiting compounds. The dehydration catalyst is therefore to periodically undergo a regeneration stage. Preferably, the reactor is used in an alternate regeneration mode, also called a swing reactor, so as to alternate the reaction and regeneration phases of said dehydration catalyst. The objective of this regeneration treatment is to burn the organic deposits as well as the radicals that contain nitrogen and sulfur, contained at the surface and within said dehydration catalyst.

The regeneration of the dehydration catalyst that is used in said stage c) is advantageously carried out by oxidation of coke and inhibiting compounds under a stream of air or in an air/nitrogen mixture, for example by using a recirculation of the combustion air with or without water so as to dilute oxygen and to control regeneration exothermy. In this case, it is possible to advantageously adjust the content of oxygen at the inlet of the reactor by a supply of air. Regeneration takes place at a pressure between atmospheric pressure (0 bar relative) and the reaction pressure. The regeneration temperature is advantageously selected from between 400 and 600° C.; it can advantageously vary during regeneration. The end of the regeneration is detected when there is no longer oxygen consumption, a sign of the total combustion of the coke.

Preferably, the effluent that is obtained from the last adiabatic reactor of stage c) is not recycled upstream from stage c), in at least one adiabatic reactor.

The effluent that is obtained from the last adiabatic reactor of stage c) is optionally sent into a gas single-phase-type exchanger in which it is "de-superheated" without being condensed by heat exchange with the vaporized and compressed feedstock that is obtained from stage b), in which it is heated. Said "de-superheated" effluent is next advantageously sent into a second gas/liquid-type exchanger in which it is partially condensed by a heat exchange that is used to evaporate the feedstock.

Stage d)

According to the invention, the effluent that is obtained from the last adiabatic reactor of stage c) undergoes a separation stage d) into an effluent that comprises ethylene at a pressure that is lower than 1 MPa and an effluent that comprises water.

Stage d) for separation of said effluent that is obtained from the last adiabatic reactor of stage c) can advantageously be implemented by any method that is known to one skilled in the art such as, for example, by a gas/liquid separation zone, and preferably a gas/liquid separation column.

The effluent that comprises ethylene at a pressure that is lower than 1 MPa next advantageously undergoes compression. Said compression makes it possible to raise the pressure of said effluent to a pressure that is advantageously between 2 and 4 MPa that is necessary for its final purification.

Preferably, the effluent that comprises ethylene that is separated at the end of stage d) is not recycled in at least one adiabatic reactor of stage c). The non-recycling of the ethylene that is separated at the end of stage d) in at least one adiabatic reactor of stage c) does not alter the selectivity of ethylene of the process according to the invention.

At least a portion of the effluent that comprises water that is obtained from stage d) is optionally recycled in separation stage d). In the case where at least a portion of the effluent that comprises water is recycled, said portion of the effluent that comprises water is advantageously cooled using cold fluid or a fluid that is obtained from the process and is preferably purified according to the known purification methods described below.

Stage e)

According to the invention, at least a portion of the effluent that comprises water that is obtained from separation stage d) undergoes a purification stage e). The purification stage e) can advantageously be implemented by any purification method that is known to one skilled in the art. By way of example, the purification stage e) can advantageously be implemented by use of ion-exchange resins, molecular sieves, membranes, by adding chemical agents for adjusting the pH, such as, for example, soda or amines, and by adding chemical agents for stabilizing the products, such as, for example, polymerization inhibitors that are selected from among bisulfites and surfactants.

At least one purified water stream and at least one unconverted ethanol stream are next separated. The separation can advantageously be implemented by any separation method that is known to one skilled in the art. By way of example, the separation can advantageously be implemented by distillation, the use of molecular sieves, membranes, vapor stripping or heat stripping or by absorption with solvent, such as, for example, glycol-containing solvents.

A stream that contains light gases, preferably acetaldehyde and methanol, can advantageously also be separated.

The use of the purified water stream that is obtained from stage e) makes it possible to separate the large majority of ethylene from water before its recycling. Thus, in the process according to the invention, ethylene is dissociated from the diluent, which makes possible the use of an inert thermal reaction diluent for the process. This also makes possible an improved energy recovery, without degrading the yield and the final ethylene selectivity.

Stage f)

According to the invention, at least a portion of the purified water stream that is obtained from stage e) is recycled upstream from stage a). At least a portion of the purified water stream that is obtained from stage e) is mixed with the ethanol feedstock that is optionally pretreated and optionally mixed with at least one unreacted ethanol stream that is obtained from stage e), upstream from evaporation stage a) of said feedstock.

The purified water stream that is obtained from stage e) plays the role of thermal reaction diluent.

The dilution of said ethanol feedstock by adding at least a portion of the purified water stream that is obtained from stage e) is carried out in a diluent to feedstock ratio by mass, advantageously between 1 and 4, for the purpose of lowering the partial ethanol pressures in the reactor(s) and making the process more selective in terms of ethylene.

At least a portion of said unreacted ethanol stream that is obtained from the purification stage e) of the effluent that comprises water is advantageously recycled and mixed, upstream from vaporization stage a), with the ethanol feedstock that is optionally pretreated and mixed with at least a portion of the purified water stream that is recycled according to stage f).

Figure 1:
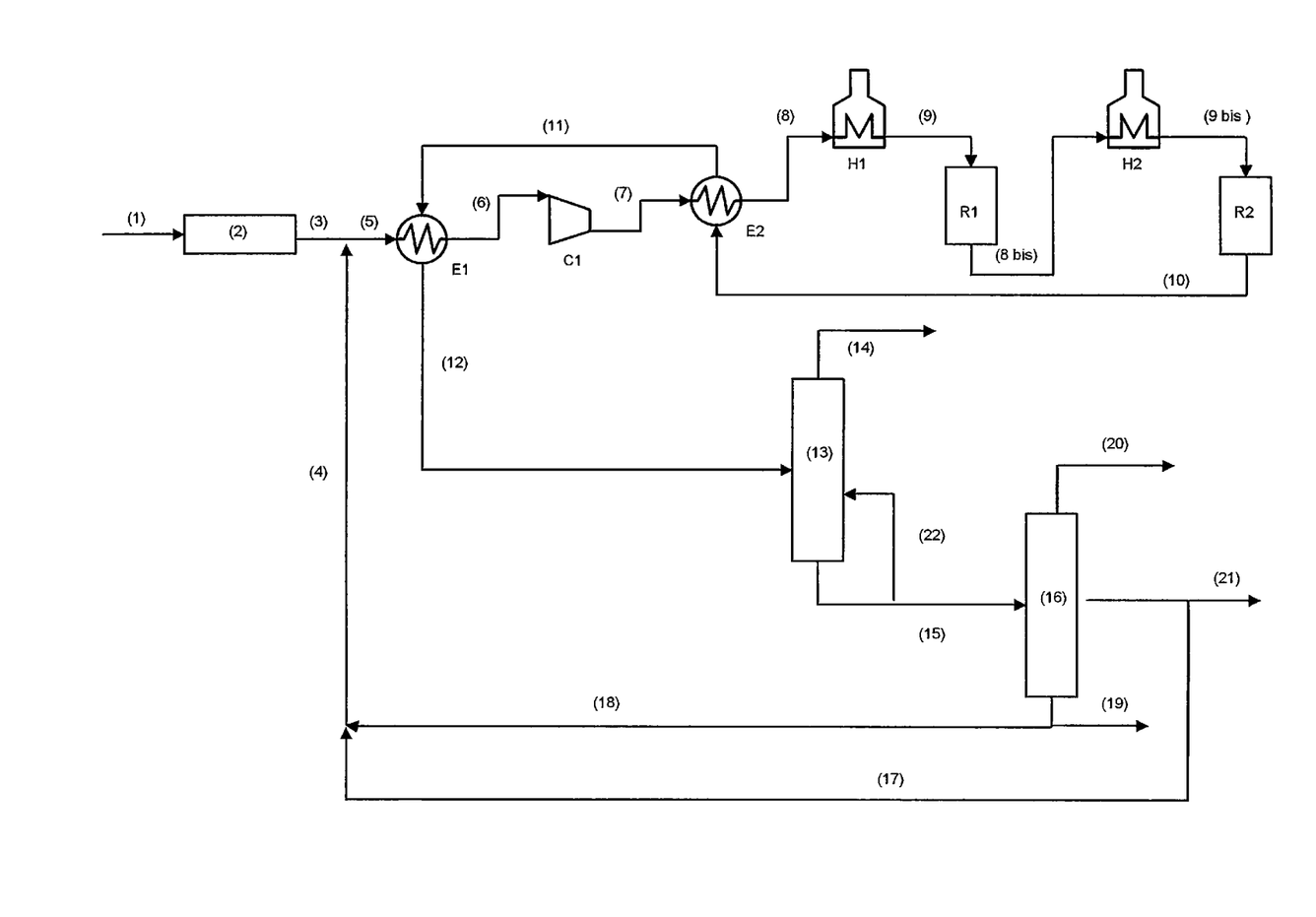
FIG. 1 diagrammatically shows the process of dehydration of ethanol in the case of the dehydration of a concentrated ethanol feedstock with recycling of at least a portion of purified water during stage f) of the process.

The ethanol feedstock is introduced into a pretreatment zone (2) via the pipe (1). The pretreated ethanol feedstock (3) is next mixed in the pipe (5) with a portion of the purified water stream that is obtained from the purification zone (16) that is recycled with reaction diluent via the pipes (18) and (4). The ethanol feedstock is also mixed with a portion of the unreacted ethanol stream that is obtained from the purification zone (16), via the pipe (17), and then (4). The pretreated ethanol feedstock that is mixed with a portion of the purified water stream that is recycled and a portion of the unreacted ethanol stream is introduced via the pipe (5) at a pressure of between 0.1 and 0.4 MPa, in a gas/liquid exchanger E1 in which said mixture undergoes heat exchange with the effluent that is obtained from the last adiabatic reactor R2 that penetrates the exchanger via the pipe (11). The latent heat or condensational enthalpy of the effluent that is obtained from the last adiabatic reactor R2 is used to vaporize the ethanol feedstock that is mixed with the purified water stream that is recycled and an unreacted ethanol stream, without an external heat supply.

The ethanol feedstock that is mixed with the purified water stream that is recycled and an unreacted ethanol stream, vaporized, is next sent via the pipe (6) into a compressor C1.

Said mixture of the feedstock and the two vaporized and compressed streams is next sent via the pipe (7) into a gas single-phase-type exchanger E2, in which said mixture is heated owing to a heat exchange with the effluent that is obtained from the last adiabatic reactor R2 that is introduced into E2 via the pipe (10). In said gas single-phase-type exchanger, said vaporized and compressed feedstock is superheated, and the effluent that is obtained, in the gaseous state, from the last adiabatic reactor R2 is "de-superheated" without being condensed.

Said mixture of the feedstock and the two streams—vaporized, compressed and heated in the gas single-phase-type exchanger E2—is next introduced into a furnace H1 via the pipe (8) in such a way as to bring it to an entrance temperature in the first adiabatic reactor R1 that is compatible with the temperature of the dehydration reaction. The effluent that is obtained from the first reactor R1 is sent into a second furnace H2 via the pipe (8b) before being introduced into the second reactor R2 via the pipe (9b).

The effluent that is obtained from the second reactor R2 next undergoes the two successive exchanges that are described above in the exchangers E2 and E1 via the pipes (10) and (11).

The effluent that is obtained from the exchanger E1 is sent via the pipe (12) into a gas/liquid separation column (13) where it is separated into an effluent that comprises ethylene (14) and an effluent that comprises water (15). A portion of the effluent that comprises water is recycled after cooling in the column (13) via the pipe (22).

The portion of the effluent that comprises non-recycled water in the column (13) is sent via the pipe (15) into a purification and separation stage (16). At least one stream of purified water (18) and (19) and at least one unconverted ethanol stream (17) and (21) are next separated. A stream that contains the light gases (20) is also separated.

A portion of said unreacted ethanol stream that is obtained from the stage (16) for purification of the effluent that comprises water is recycled via the pipe (17) and is mixed with at least a portion of the purified water stream that is recycled via the pipe (18) into the pipe (4). The mixture of these two streams is mixed upstream from the exchanger E1, with the pretreated ethanol feedstock (3).

The following examples illustrate the invention without limiting its scope.

EXAMPLES

Example 1

In Accordance with the Invention

Example 1 illustrates a process according to the invention in which stage c) is implemented in an adiabatic reactor.

The ethanol feedstock under consideration is produced by fermentation of wheat, without extracting gluten, by a dry-milling-type process according to the English term.

The ethanol feedstock whose composition is provided in Column 1 of Table 1 is pretreated on a resin TA 801 at a temperature of 140° C. The characteristics of the pretreated ethanol feedstock are also provided in Column 2 of Table 1.

Stage a)

Said pretreated ethanol feedstock is introduced, at a flow rate of 46,187 kg/h, into a mixture with 114,547 kg/h of recycled purified water that is obtained from stage e) and with 132 kg/h of unconverted ethanol that is obtained from stage e), in an exchanger E1 at a pressure that is equal to 0.31 MPa.

The stream of purified water that is obtained from stage e) plays the role of thermal reaction diluent. The dilution of said ethanol feedstock by adding a portion of the purified water stream obtained from stage e) is carried out in a diluent to feedstock ratio by mass that is equal to 2.5.

TABLE 1

Characteristics of the Ethanol Feedstock Before and After Pretreatment

|  | (1) | (2) | Unit |
| --- | --- | --- | --- |
| Ethanol Content | 91.9 | 91.9 | % by Weight |
| Acetaldehyde | 0.0169 | 0.0169 | % by Weight |
| Aldehydes | 0.0175 | 0.0175 | % by Weight |
| Esters | 0.003 | 0.003 | % by Weight |
| Higher Alcohols | 0.2144 | 0.2144 | % by Weight |
| Methanol | 0.0038 | 0.0038 | % by Weight |
| 1-Propanol | 0.0604 | 0.0604 | % by Weight |
| 2-Methyl-1 Propanol | 0.0551 | 0.0551 | % by Weight |
| 1 Butanol | 0.0018 | 0.0018 | % by Weight |
| 2-Methyl-1 Butanol | 0.0256 | 0.0256 | % by Weight |
| 3-Methyl-1 Butanol | 0.0715 | 0.0715 | % by Weight |
| Nitrogen Compounds | 0.005 | 0 | % by Weight |
| Water Content | 7.4156 | 7.4156 | % by Weight |

(1): Feedstock Ethanol
(2): After Pretreatment

For the sake of simplicity, the description of the impurities in the pretreated feedstock was removed from the text below.

In stage a), the majority of the latent heat of the aqueous phase of the effluent that is obtained from the adiabatic reactor of stage c) is recovered for vaporizing the mixture of the feedstock and two other streams, without an external heat supply. Thus, 90.1% of the water that is contained in said effluent that is obtained from the adiabatic reactor of stage c)

is in liquid aqueous form. Thus, 88.5 MW is exchanged between the mixture of the feedstock and two other streams and the effluent of the reactor.

The temperature at the beginning of the vaporization of said feedstock is equal to 126° C. (at 0.27 MPa) and the final condensation temperature of said effluent that is obtained from the adiabatic reactor is—the effluent is −117° C. (at 0.41 MPa) [sic].

Stage b)

The mixture of the feedstock and two other streams, vaporized, obtained from the exchanger, is next compressed in a radial compressor with an integrated multiplier such that the pressure of said mixture of the feedstock and two other streams, vaporized at the end of the compression, is equal to 0.63 MPa.

The mixture of the feedstock and two other streams, vaporized and compressed, is next heated in a gas single-phase-type exchanger E2, owing to a heat exchange with the effluent that is obtained from the adiabatic reactor of stage c). In said gas single-phase-type exchanger, said mixture of the feedstock and two other streams, vaporized and compressed, is superheated to a temperature of 345° C. and the effluent that is obtained, in the gaseous state, of the adiabatic reactor of stage c) is "de-superheated" without being condensed and has a temperature of 269° C.

Stage c)

Said mixture of the feedstock and two other streams—vaporized, compressed and heated in said gas single-phase-type exchanger—is next introduced into a furnace in such a way as to bring it to an entrance temperature in said adiabatic reactor that is compatible with the temperature of the dehydration reaction, i.e., at a temperature of 500° C.

Said mixture of the feedstock and two other streams—vaporized, compressed and heated—is introduced into the adiabatic reactor at an entrance pressure of 0.53 MPa.

The adiabatic reactor contains a fixed bed of dehydration catalyst, with said catalyst comprising 80% by weight of ZSM-5 zeolite that is treated with $H_3PO_4$ in such a way that the $P_2O_5$ content is 3.5% by weight.

The temperature and pressure conditions of the streams entering and exiting from the adiabatic reactor of stage c) are provided in Table 2:

TABLE 2

Operating Conditions of Dehydration Stage c).

| | Unit | Entrance | Exit |
|---|---|---|---|
| Pressure | MPa | 0.53 | 0.50 |
| Hourly Speed by Weight | $h^{-1}$ | 7 | 7 |
| Reaction Temperature | ° C. | 500 | 384 |

The conversion of the ethanol feedstock in stage c) is 99.4%.

Stage d)

The effluent that is obtained from the adiabatic reactor of stage c) next undergoes the two heat exchanges described above and is sent into a gas/liquid separation column. An effluent that comprises ethylene at a pressure that is equal to 0.39 MPa is separated as well as an effluent that comprises water. This separation is carried out by the use of a gas/liquid separation column, with recycling of the water that is produced at the bottom of the column toward the top of the column and after cooling and injection of neutralizing agent.

The effluent that comprises ethylene next undergoes compression for raising its pressure to 2.78 MPa before its final purification. The separated ethylene is not recycled in said adiabatic reactor.

Stage e)

A purified water stream and an unconverted ethanol stream as well as a stream that contains light gases are next separated by conventional low-pressure distillation from the raw water.

Stage f)

A portion of the purified water stream and a portion of the unconverted ethanol stream are recycled upstream from vaporization stage a) in the proportions that are described in stage a).

Information regarding the different streams, in kg/h, is given in Tables 3 and 4:

TABLES 3 AND 4

Composition of the Primary Streams.

| | | Description of the Stream | | | |
|---|---|---|---|---|---|
| | | Pretreated Ethanol Feedstock | Stream Entering Into R1 | Stream Exiting From R1 | Effluent Comprising Ethylene |
| | | Stream No. Corresponding to the FIG. | | | |
| | | 3 | 9 | 10 | 14 |
| Total Mass Flow Rate | kg/h | 46,187 | 160,866 | 160,866 | 26,076 |
| Mass Flow Rate, by Components | kg/h | | | | |
| Ethylene | | 0 | 0 | 25,154 | 25,124 |
| Ethane | | 0 | 0 | 21 | 21 |
| C3 | | 0 | 0 | 88 | 88 |
| C4 | | 0 | 0 | 504 | 503 |
| Oxidized Compounds (Other than Ethanol) | | 0 | 0 | 110 | 27 |
| Ethanol | | 42,446 | 42,685 | 267 | 6 |
| $H_2O$ | | 3,741 | 118,182 | 134,722 | 307 |

| | | Description of the Stream | | | | |
|---|---|---|---|---|---|---|
| | | Effluent That Comprises Water | Unconverted Ethanol Recycling | Recycled Purified Water | Purged Water | Light Gases |
| | | Stream No. Corresponding to the FIG. | | | | |
| | | 15 | 17 | 18 | 19 | 20 |
| Total Mass Flow Rate | kg/h | 134,790 | 132 | 114,547 | 19,997 | 114 |
| Mass Flow Rate, By Components | kg/h | | | | | |
| Ethylene | | 31 | 0 | 0 | 0 | 30.9 |
| Ethane | | 0 | 0 | 0 | 0 | 0.0 |
| C3 | | 0 | 0 | 0 | 0 | 0.1 |
| C4 | | 1 | 0 | 0 | 0 | 0.5 |
| Oxidized Compounds (Other than Ethanol) | | 83 | 0 | 0 | 0 | 83 |
| Ethanol | | 261 | 126 | 113 | 22 | 0.0 |
| $H_2O$ | | 134,415 | 6 | 114,434 | 19,975 | 0.0 |

The compounds C3 and C4 are C3 and C4 hydrocarbon compounds.

The selectivity of the process in terms of ethylene is 97%.

It is calculated in the following way: (Ethylene that is contained in the effluent that comprises ethylene)/(0.61*amount of converted ethanol) or the amount of converted ethanol is the ethanol that is contained in the pretreated ethanol feedstock that is subtracted from the ethanol that is contained in the streams of purged water and in the effluent that comprises ethylene. 0.61 g is the maximum amount of ethylene that is obtained by dehydrating 1 g of pure ethanol.

Information on the energy balance of the diagram according to Example 1 in accordance with the invention is given in Table 5:

TABLE 5

Energy Balance

| Energy Exchanged Inside the System | | Energy Provided to the System by an External Supply | | |
|---|---|---|---|---|
| Amount of Heat Exchanged in the First Exchanger (E1) MW | Amount of Heat Exchanged in the Second Exchanger (E2) MW | Amount of Heat Exchanged in the Furnace MW | Electricity Required for Compression MW | Amount of Heat Extracted on the Gas/Liquid Separation Column MW |
| 88.5 | 10.8 | 15.4 | 8.4 | 13.8 |

The estimation of the primary energy consumption was carried out by using the following bases:
Effectiveness of 0.8 on the furnaces
Effectiveness of 0.375 on the production of electricity.

The diagram according to Example 1 in accordance with the invention has an equivalent primary energy consumption or a specific consumption of 6 GJ equivalent per ton of ethylene that is produced.

Example 2

In Accordance with the Invention

Example 2 illustrates a process according to the invention in which stage c) is implemented in two adiabatic reactors.
Stage a)

The same pretreated ethanol feedstock as the one that is used in Example 1 is introduced with a flow rate of 46,187 kg/h into an exchanger E1 at a pressure that is equal to 0.31 MPa, mixed with 114,549 kg/h of recycled purified water and with 131 kg/h of unconverted ethanol, obtained from stage e).
Stage b)

The heat exchange that is described in Example 1 takes place and the mixing of the feedstock and the two streams, vaporized, is next compressed in a compressor of the same type as that of Example 1 in such a way that the pressure of said mixture of the feedstock and the two streams, vaporized at the end of the compression, is equal to 0.69 MPa. 90.2% of the water that is contained in the effluent that is obtained from the last reactor is in liquid aqueous form. Thus, 88.9 MW is exchanged between mixing the feedstock and the two streams and the effluent that is obtained from the last reactor.

The temperature at the beginning of the evaporation of said feedstock is equal to 126° C. (at 0.27 MPa) and the final condensation temperature of said effluent that is obtained from the adiabatic reactor is—the effluent is −117° C. (at 0.41 MPa) [sic].
Stage c)

The mixture of the feedstock and the two streams, vaporized and compressed, is next heated in a gas single-phase-type exchanger E2 owing to a heat exchange with the effluent that is obtained from the second adiabatic reactor of stage c). In said gas single-phase-type exchanger, the mixture of the feedstock and the two streams, vaporized and compressed, is superheated to a temperature of 353° C., and the effluent that is obtained, in the gaseous state, of the adiabatic reactor of stage c) is "de-superheated" without being condensed and has a temperature of 275° C.

The mixture of the feedstock and the two streams—vaporized, compressed and heated in said gas single-phase-type exchanger—is next introduced into a furnace in such a way as to bring it to an entrance temperature in the first adiabatic reactor that is compatible with the temperature of the dehydration reaction, i.e., to a temperature of 400° C.

The mixture of the feedstock and the two streams—vaporized, compressed and heated—is introduced into the first adiabatic reactor at an entrance pressure of 0.62 MPa.

The effluent that is obtained from the first adiabatic reactor exits from said first reactor at a temperature of 318° C. and is next introduced into a furnace in such a way that the entrance temperature of said effluent in the second adiabatic reactor is 405° C. Said effluent has an entrance pressure in said second reactor of 0.53 MPa.

The effluent that is obtained from the second adiabatic reactor exits from said second adiabatic reactor at a temperature of 380° C. and at a pressure of 0.50 MPa.

The two adiabatic reactors each contain a fixed dehydration catalyst bed, whereby said catalyst is identical in the two reactors and identical to the one that is used in Example 1.

The temperature and pressure conditions of the streams that enter and exit from the adiabatic reactors of stage c) are provided in Table 6:

TABLE 6

Operating Conditions of Dehydration Stage c).

| | | Reactor 1 | | Reactor 2 | |
|---|---|---|---|---|---|
| | Unit | Entrance | Exit | Entrance | Exit |
| Pressure | MPa | 0.59 | 0.56 | 0.53 | 0.50 |
| Hourly Speed by Weight | h$^{-1}$ | 14 | | 14 | |
| Reaction Temperature | ° C. | 400 | 318 | 405 | 380 |

The conversion of the ethanol feedstock at the end of stage c) is 99.4%.
Stage d)

The effluent that is obtained from the second adiabatic reactor of stage c) next undergoes the two heat exchanges described above and is sent into a gas/liquid separation column. An effluent that comprises ethylene at a pressure that is equal to 0.39 MPa is separated as well as an effluent that comprises water. This separation is carried out by use of a gas/liquid separation column, with recycling of the water that is produced at the bottom of the column toward the top of the column after cooling and injection of a neutralizing agent.

The effluent that comprises ethylene next advantageously undergoes compression for raising its pressure to 2.78 MPa before its final purification. The separated ethylene is not recycled in the first or the second adiabatic reactor.
Stage e)

A purified water stream and an unconverted ethanol stream as well as a stream containing light gases are next separated by conventional low-pressure distillation of the raw water.
Stage f)

A portion of the purified water stream and a portion of the unconverted ethanol stream are recycled upstream from evaporation stage a) in the proportions that are described in stage a).

Information regarding the different streams, in kg/h, is given in Tables 7 and 8:

TABLES 7 AND 8

| | | Composition of the Primary Streams. | | | | |
|---|---|---|---|---|---|---|
| | | Description of the Stream | | | | |
| | | Pretreated Ethanol Feedstock | Stream Entering into R1 | Stream Entering into R2 | Stream Exiting from R2 | Effluent that Comprises Ethylene |
| | | Stream No. | | | | |
| | | 3 | 9 | 9b | 10 | 14 |
| Total Mass Flow Rate | kg/h | 46,187 | 160,867 | 160,867 | 160,867 | 26,076 |
| Mass Flow Rate, by Components | kg/h | | | | | |
| Ethylene | | 0 | 0 | 17,929 | 25,155 | 25,123 |
| Ethane | | 0 | 0 | 10 | 21 | 21 |
| C3 | | 0 | 0 | 11 | 88 | 88 |
| C4 | | 0 | 0 | 137 | 504 | 503 |
| Oxidized Compounds (Other than Ethanol) | | 0 | 0 | 599 | 110 | 27 |
| Ethanol | | 42,446 | 42,685 | 12,183 | 267 | 6 |
| $H_2O$ | | 3,741 | 118,182 | 129,998 | 134,727 | 307 |

| | | Description of the Stream | | | | |
|---|---|---|---|---|---|---|
| | | Effluent that Comprises Water | Unconverted Ethanol Recycling | Recycled Purified Water | Purged Water | Light Gases |
| | | Stream No. | | | | |
| | | 15 | 17 | 18 | 19 | 20 |
| Total Mass Flow Rate | kg/h | 134,790 | 131 | 114,549 | 19,996 | 114 |
| Mass Flow Rate, by Components | kg/h | | | | | |
| Ethylene | | 31 | 0 | 0 | 0 | 31 |
| Ethane | | 0 | 0 | 0 | 0 | 0 |
| C3 | | 0 | 0 | 0 | 0 | 0 |
| C4 | | 1 | 0 | 0 | 0 | 1 |
| Oxidized Compounds (Other than Ethanol) | | 83 | 0 | 0 | 0 | 83 |
| Ethanol | | 261 | 125 | 113 | 22 | 0 |
| $H_2O$ | | 134,415 | 6 | 114,436 | 19,974 | 0 |

The selectivity of the process in terms of ethylene is 97%. It is calculated in the same way as for Example 1.

Information regarding the energy balance of the diagram according to Example 1 according to the invention is given in Table 9:

TABLE 9

| Energy Balance | | | | | |
|---|---|---|---|---|---|
| Energy Exchanged Inside the System | | Energy Provided to the System by an External Supply | | | |
| Amount of Heat Exchanged in the First Exchanger E1 MW | Amount of Heat Exchanged in the Second Exchanger E2 MW | Amount of Heat Exchanged in the First Furnace MW | Amount of Heat Exchanged in the Second Furnace MW | Electricity Required for Compression MW | Amount of Heat Extracted on the Gas/Liquid Separation Column MW |
| 88.9 | 9.9 | 4.6 | 8.4 | 9.5 | 14.0 |

The estimation of the primary energy consumption was carried out by using the same bases as for Diagram 1.

The diagram according to Example 2 in accordance with the invention has an equivalent primary energy consumption or specific consumption of 6 GJ equivalent per ton of ethylene produced.

Example 3

For Comparison

Example 3 illustrates a process in which the dehydration reaction is implemented in an adiabatic reactor and in which the feedstock, mixed with an unconverted ethanol stream and a purified water stream, is introduced at low pressure into the vaporization stage a), and said mixture, vaporized, at the outlet of the exchanger does not undergo compression stage b). In this example, the separated ethylene is not recycled in said adiabatic reactor that contains the dehydration catalyst.

The same pretreated ethanol feedstock as that used in Example 1 is introduced, with a flow rate of 46,066 kg/h, into an exchanger at a pressure that is equal to 0.65 MPa, mixed with 114,553 kg/h of recycled purified water and with 131 kg/h of unconverted ethanol that is obtained from stage e). The mixture of the ethanol feedstock with the two other streams described above is partially vaporized by heat exchange between said mixture and the effluent that is obtained from the adiabatic reactor. Only a portion of the latent condensation heat of the aqueous phase of the effluent can be used to partially vaporize said mixture of the ethanol feedstock with the other two streams. Thus, only 33.3% by weight of said mixture is vaporized and only 12% of the aqueous effluent is condensed, which corresponds to an exchanged heat amount of 31.8 MW. So as to totally vaporize said mixture, an additional amount of heat of 58.2 MW is to be provided by an outside heat source: said partially vaporized mixture is next totally vaporized in an evaporator-type exchanger, using the vapor as a coolant.

Said partially vaporized mixture, that is then vaporized in said evaporator-type exchanger, is next introduced into a furnace in such a way as to bring it to an entrance temperature in said adiabatic reactor that is compatible with the temperature of the dehydration reaction, i.e., at a temperature of 500° C.

Said vaporized and heated feedstock is introduced into the adiabatic reactor at an entrance pressure of 0.53 MPa.

The adiabatic reactor contains a fixed dehydration catalyst bed, whereby said catalyst is identical to that which is used in Example 1.

The temperature and pressure conditions in said adiabatic reactor are as follows:

TABLE 10

Operating Conditions of Dehydration Stage c).

|  | Unit | Entrance | Exit |
|---|---|---|---|
| Pressure | MPa | 0.53 | 0.50 |
| Hourly Speed by Weight | h$^{-1}$ | 7 | 7 |
| Reaction Temperature | ° C. | 500 | 383 |

The conversion of the ethanol feedstock is 99.4%

The effluent that is obtained from the adiabatic reactor of stage c) next undergoes the heat exchange described above: it is cooled up to 144° C. and should be cooled in an exchanger that uses an outside refrigerant fluid for reaching 117° C. before being sent into a gas/liquid separation column. This exchanger is a cooler that operates with water. An amount of heat of 68 MW should thus be exchanged between the effluent of the reactor and the refrigerant fluid. An effluent that comprises ethylene at a pressure that is equal to 0.38 MPa is separated as well as an effluent that comprises water. This separation is carried out by the use of a gas/liquid separation column, with recycling of the water that is produced at the bottom of the column toward the top of the column after cooling and injection of neutralizing agent.

The effluent that comprises ethylene next advantageously undergoes compression for raising its pressure to 2.78 MPa before its final purification. The separated ethylene is not recycled in said adiabatic reactor.

A purified water stream and an unconverted ethanol stream as well as a stream that contains light gases are next separated by conventional low-pressure distillation of the raw water.

A purified water stream and an unconverted ethanol stream are next separated by conventional low-pressure distillation of raw water.

A portion of the purified water stream and a portion of the unconverted ethanol stream are recycled upstream from vaporization stage a).

Information regarding the different streams, in kg/h, is provided in Tables 11 and 12:

TABLES 11 AND 12

Composition of the Primary Streams.

| | | Description of the Stream | | | |
|---|---|---|---|---|---|
| | | Pretreated Ethanol Feedstock | Stream Entering into R1 | Stream Exiting from R1 | Effluent that Comprises Ethylene | Effluent that Comprises Water |
| Total Mass Flow Rate | kg/h | 46,066 | 160,750 | 160,750 | 26,015 | 134,734 |
| Mass Flow Rate, by Components | kg/h | | | | | |
| Ethylene | | 0 | 0 | 25,088 | 25,057 | 31 |
| Ethane | | 0 | 0 | 21 | 21 | 0 |
| C3 | | 0 | 0 | 88 | 88 | 0 |
| C4 | | 0 | 0 | 502 | 502 | 1 |
| Oxidized Compounds (Other than Ethanol) | | 0 | 0 | 110 | 28 | 82 |
| Ethanol | | 42,335 | 42,572 | 266 | 6 | 260 |
| H$_2$O | | 3,731 | 118,178 | 134,675 | 314 | 134,361 |

TABLES 11 AND 12-continued

Composition of the Primary Streams.

| | | Description of the Stream | | | |
|---|---|---|---|---|---|
| | | Unconverted Ethanol Recycling | Recycled Purified Water | Purged Water | Light Gases |
| Total Mass Flow Rate | kg/h | 131 | 114,553 | 19,936 | 113 |
| Mass Flow Rate, by Components | kg/h | | | | |
| Ethylene | | 0 | 0 | 0 | 31 |
| Ethane | | 0 | 0 | 0 | 0 |
| C3 | | 0 | 0 | 0 | 0 |
| C4 | | 0 | 0 | 0 | 1 |
| Oxidized Compounds (Other than Ethanol) | | 0 | 0 | 0 | 82 |
| Ethanol | | 125 | 113 | 21 | 0 |
| $H_2O$ | | 6 | 114,440 | 19,915 | 0 |

The selectivity of the process in terms of ethylene is 97%. It is calculated in the same way as for Example 1.

Information regarding the energy balance of the diagram according to Example 3 that is not in accordance with the invention is given in Table 13:

TABLE 13

Energy Balance

| Energy Exchanged Inside the System Amount of Heat Exchanged on the $1^{st}$ Exchanger MW | Energy Provided to the System by an External Supply | | | |
|---|---|---|---|---|
| | Amount of Heat Exchanged on the Evaporator MW | Amount of Heat Exchanged on the Furnace MW | Amount of Heat Extracted on the Cooler MW | Amount of Heat Extracted on the Gas/Liquid Separation Column MW |
| 31.9 | 58.2 | 33.0 | 68.0 | 13.6 |

The estimation of the primary energy consumption was carried out by using the same bases as for diagram 1, by considering in addition an effectiveness of 0.9 on the vapor production.

This diagram 3 has an equivalent primary energy consumption or a specific consumption of 15.2 GJ equivalent per ton of ethylene that is produced. The vaporization of the feedstock that is mixed with an unconverted ethanol stream and a purified water stream, carried out in diagram 1 of Example 1 according to this invention, at low pressure, makes it possible to reduce in a significant way the equivalent primary energy consumption: Diagram 1 had a primary energy consumption of 6 GJ equivalent per ton of ethylene.

Example 4

For Comparison

Example 4 illustrates a process in which the dehydration reaction is implemented in an adiabatic reactor and in which the feedstock, mixed with an unconverted ethanol stream and with a purified water stream, is introduced into vaporization stage a) and said mixture, vaporized, at the outlet of the exchanger, does not undergo compression stage b). In this example, a portion of the effluent that is obtained from the adiabatic reactor, comprising ethylene and water, is recycled in said adiabatic reactor that contains the dehydration catalyst.

Example 4 is based on the fact that a portion of the effluent that is obtained from the adiabatic reactor, comprising ethylene and water, is compressed and recycled at the inlet of the first reactor, this for the purpose of recycling a portion of the coolant that is the water that is directly in vapor form without condensation and revaporization. This recycling contains ethylene, however, and consequently secondary reactions of oligomerization, hydrogen transfer, and disproportionation of the olefins will take place in a larger amount on the reactor, leading to an overall loss of ethylene production on the reactor and therefore a reduction in ethylene selectivity.

The same pretreated ethanol feedstock as the one used in Example 1 is introduced at a rate of 46,065 kg/h in an exchanger at a pressure that is equal to 0.65 MPa, mixed with 49,241 kg/h of recycled purified water and with 205 kg/h of unconverted ethanol. Said mixture of the ethanol feedstock mixed with the purified water stream and the unconverted ethanol stream is partially vaporized by heat exchanger with the effluent that is obtained from the adiabatic reactor. Only a portion of the latent condensation heat of the aqueous phase of the effluent can be used for partially vaporizing said mixture. Thus, only 42.4% by weight of said mixture is vaporized and only 17% by weight of the aqueous effluent is condensed, which corresponds to an amount of heat exchanged that is 21.3 MW.

Said partially vaporized mixture is next mixed with a portion of the effluent that is obtained from the adiabatic reactor that comprises ethylene and water, previously compressed, whose flow rate is 20,000 kg/h. The supply of heat that is linked to said recycled and compressed effluent is not adequate to vaporize the entire mixture of the ethanol feedstock mixed with the purified water stream and the unconverted ethanol stream: 88% by weight of said mixture is vaporized. So as to totally vaporize said mixture, it is necessary to provide an additional 12.8 MW by an external heat source: said partially vaporized mixture is next vaporized totally in an evaporator-type exchanger that uses vapor as a coolant.

Said mixture that is vaporized and heated in said evaporator-type exchanger is next introduced into a furnace in such a way as to bring it to an entrance temperature in said adiabatic reactor that is compatible with the temperature of the dehydration reaction, i.e., to a temperature of 476° C.

Said vaporized and heated feedstock is introduced into the adiabatic reactor at an entrance pressure of 0.53 MPa.

The adiabatic reactor contains a fixed dehydration catalyst bed, whereby said catalyst is identical to the one that is used in Example 1.

The temperature and pressure conditions in said adiabatic reactor are as follows:

TABLE 14

Operating Conditions.

| | Unit | Entrance | Exit |
|---|---|---|---|
| Pressure | MPa | 0.53 | 0.50 |
| Hourly Speed by Weight | $h^{-1}$ | 7 | 7 |
| Reaction Temperature | °C. | 476 | 393 |

The conversion of the ethanol feedstock is 98.8%.

The effluent that is obtained from the adiabatic reactor next undergoes the heat exchange that is described above and is cooled to 117° C. by an outside source before being sent into a gas/liquid separation column. This exchanger can be a cooler that operates with water. An amount of heat of 30.9 MW should thus be exchanged between the effluent of the reactor and the refrigerant fluid. An effluent that comprises ethylene at a pressure that is equal to 0.43 MPa is separated as well as an effluent that comprises water. This separation is carried out by the use of a gas/liquid separation column, with recycling of the water that is produced at the bottom of the column to the top of the column after cooling and injection of neutralizing agent.

The effluent that comprises ethylene next advantageously undergoes compression for raising its pressure to 2.78 MPa before its final purification. The separated ethylene is not recycled in said adiabatic reactor.

A purified water stream and an unconverted ethanol stream as well as a stream that contains light gases are next separated by conventional low-pressure distillation of the raw water.

A portion of the purified water stream and a portion of the unconverted ethanol stream are recycled upstream from the vaporization stage a).

Information regarding the different streams, in kg/h, is given in Table 15:

TABLE 15

Composition of the Primary Streams.

| | | Description of the Streams | | | | |
|---|---|---|---|---|---|---|
| | | Pretreated Ethanol Feedstock | Exchanger Entrance Recombined Load | Recycling of the Effluent Obtained from the Reactor | Stream Entering the Reactor | Stream Exiting from the Reactor |
| Total Mass Flow Rate | kg/h | 46,065 | 95,511 | 89,742 | 185,252 | 185,252 |
| Mass Flow Rate, by Components | kg/h | | | | | |
| Ethylene | | 0 | 0 | 20,000 | 20,000 | 41,283 |
| Ethane | | 0 | 0 | 27 | 27 | 56 |
| C3 | | 0 | 0 | 1,187 | 1,187 | 2,450 |
| C4 | | 0 | 0 | 2,655 | 2,655 | 5,480 |
| Oxidized Compounds (Other than Ethanol) | | 0 | 0 | 112 | 112 | 231 |
| Ethanol | | 42,334 | 42,578 | 245 | 42,823 | 518 |
| H$_2$O | | 3,731 | 52,932 | 65,242 | 118,175 | 134,669 |
| C4+ | | 0 | 0 | 274 | 274 | 566 |

| | | Description of the Streams | | | | |
|---|---|---|---|---|---|---|
| | | Effluent Going to the Exchanger | Effluent that Comprises Ethylene | Effluent that Comprises Water | Recycling of Unconverted Ethanol | Recycled Purified Water |
| Total Mass Flow Rate | kg/h | 95,509 | 25,978 | 69,531 | 205 | 49,241 |
| Mass Flow Rate, by Components | kg/h | | | | | |
| Ethylene | | 21,283 | 21,261 | 22 | 0 | 0 |
| Ethane | | 29 | 29 | 0 | 0 | 0 |
| C3 | | 1,263 | 1,262 | 1 | 0 | 0 |
| C4 | | 2,825 | 2,823 | 2 | 0 | 0 |
| Oxidized Compounds (Other than Ethanol | | 119 | 46 | 73 | 0 | 0 |

TABLE 15-continued

| Composition of the Primary Streams. | | | | | |
|---|---|---|---|---|---|
| Ethanol | 273 | 10 | 263 | 196 | 48 |
| $H_2O$ | 69,426 | 259 | 69,168 | 9 | 49,193 |
| C4+ | 292 | 290 | 2 | 0 | 0 |

| | | Description of the Streams | |
|---|---|---|---|
| | | Purged Water | Light Gases |
| Total Mass Flow Rate | kg/h | 19,985 | 100 |
| Mass Flow Rate, by Components | kg/h | | |
| Ethylene | | 0 | 22 |
| Ethane | | 0 | 0 |
| C3 | | 0 | 1 |
| C4 | | 0 | 2 |
| Oxidized Compounds (Other than Ethanol) | | 0 | 73 |
| Ethanol | | 19 | 0 |
| $H_2O$ | | 19,966 | 0 |
| C4+ | | 0 | 2 |

The selectivity of the process in terms of ethylene is 82%. It is calculated in the same way as for Example 1. The loss of selectivity that is linked to the recycling of the effluent that is obtained from the adiabatic reactor comprising ethylene and water is noted, with the preceding diagrams not implementing the recycling of said effluent that comprises ethylene, making it possible to obtain selectivity in terms of ethylene of 97%.

Information regarding the energy balance of the diagram according to Example 4 that is not in accordance with the invention is given in Table 16:

TABLE 16

| Energy Balance | | | | | |
|---|---|---|---|---|---|
| Energy Exchanged Inside the System | Energy Provided to the System by an External Supply | | | | |
| Amount of Heat Exchanged on the First Exchanger MW | Amount of Heat Exchanged on the Evaporator MW | Amount of Heat Exchanged on the Furnace MW | Electricity Required for the Compressor MW | Amount of Heat Extracted on the Cooler MW | Amount of Heat Extracted on the Gas/Liquid Separation Column MW |
| 21.3 Internal Source | 12.8 External Source | 36.7 External Source | 0.65 External Source | 30.8 External Source | 11.9 External Source |

The estimation of the primary energy consumption was carried out by using the same bases as for Diagram 1, by considering in addition an effectiveness of 0.9 on the vapor production.

This diagram 4 has an equivalent primary energy consumption or a specific consumption of 10.5 GJ equivalent per ton of ethylene that is produced. The vaporization of the feedstock mixed with an unconverted ethanol stream and a purified water stream, carried out in Diagram 1 of Example 1 according to this invention, at low pressure, makes it possible to reduce in a significant way the equivalent primary energy consumption: Diagram 1 had a primary energy consumption of 6 GJ equivalent per ton of ethylene.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. Nos. 11/02.274, filed 21 Jul. 2011, and 11/02.482, filed on 8 Aug. 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for dehydration of an ethanol feedstock into ethylene comprising:
   a) vaporizing of said ethanol feedstock in a mixture with at least a portion of a purified water stream recycled from f) in an exchanger owing to a heat exchange with the effluent that is obtained from a last adiabatic reactor, introducing said ethanol feedstock in a mixture with at least a portion of said purified water stream that is recycled into said vaporization at a pressure of between 0.1 and 0.4 MPa, b) compressing vaporized ethanol feedstock purified water mixture, in a compressor, c) introducing compressed vaporized ethanol feedstock purified water mixture, at an entrance temperature of between 350 and 500° C. and at an entrance pressure of between 0.2 and 1.3 MPa, in at least one adiabatic reactor that contains at least one dehydration catalyst and in which dehydration reaction takes place, d) separating effluent that is obtained from a last adiabatic reactor of stage c) in an effluent that comprises ethylene an effluent that comprises water, wherein the effluent that comprises ethylene is at a pressure that is lower than 1 MPa, e) purifying at least a portion of the effluent comprising water that is obtained from d) and separating at least one purified water stream and at least one unconverted ethanol stream, f) recycling at least a portion of the purified water stream that is obtained from e), upstream from a).

2. The process according to claim 1, in which said ethanol feedstock is an ethanol feedstock that is produced from a renewable source that is obtained from biomass.

3. The process according to claim 1, in which said ethanol feedstock undergoes a pretreatment prior to the vaporization a).

4. The process according to claim 1, in which at least one unreacted ethanol stream that is obtained from e) is also introduced into the exchanger of vaporization a).

5. The process according to claim 1, in which said ethanol feedstock that is mixed with at least a portion of the purified water stream recycled from f) is introduced into a) vaporization at a pressure that is lower than the pressure of effluent at the outlet of the last adiabatic reactor.

6. The process according to claim 1, in which the ethanol feedstock mixed with at least a portion of the purified water stream recycled from f), and vaporized at the end of compression b), has a pressure between 0.2 and 1.3 MPa.

7. The process according to claim 1, in which said ethanol feedstock that is mixed with at least a portion of the purified water stream that is recycled from f) obtained from compression b), is heated in a gas single-phase-type exchanger, undergoing heat exchange with effluent that is obtained from the last adiabatic reactor of c).

8. The process according to claim 1, in which effluent that is obtained from the last adiabatic reactor of c) has a temperature of between 270 and 420° C. at the outlet of the last adiabatic reactor of c).

9. The process according to claim 1, in which the effluent that is obtained from the last adiabatic reactor of c) has a pressure of between 0.1 and 1.1 MPa at the outlet of the last adiabatic reactor of c).

10. The process according to claim 1, in which the effluent that is obtained from the last adiabatic reactor of c) is not recycled upstream from c), in at least one adiabatic reactor.

11. The process according to claim 1, in which dehydration in c) is carried out in one or two reactors.

12. The process according to claim 1, in which said dehydration catalyst that is used in c) is an amorphous acid catalyst or a zeolitic acid catalyst.

13. The process according to claim 1, in which at least a portion of unreacted ethanol stream that is obtained from e) is recycled and mixed with ethanol feedstock upstream from a).

14. The process according to claim 1, in which said ethanol feedstock is a concentrated hydrated ethanol feedstock.

15. The process according to claim 14, in which said concentrated ethanol feedstock comprises ethanol between 35 and 99.9% by weight.

16. The process according to claim 15, in which said concentrated ethanol feedstock comprises ethanol between 35 and 96% by weight.

* * * * *